United States Patent
Murashita (10) Patent No.: US 9,039,620 B2
(45) Date of Patent: May 26, 2015

(54) ULTRASOUND DIAGNOSTIC APPARATUS (75) Inventor: Masaru Murashita, Tokyo (JP)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 738 days.

(21) Appl. No.: 12/174,082

(22) Filed: Jul. 16, 2008

(65) Prior Publication Data
US 2009/0024033 A1 Jan. 22, 2009

(30) Foreign Application Priority Data

Jul. 17, 2007 (JP) ................. 2007-185566

(51) Int. Cl.
*A61B 8/00* (2006.01)
*A61B 8/14* (2006.01)
*A61B 8/06* (2006.01)
*A61B 8/13* (2006.01)
*A61B 8/08* (2006.01)

(52) U.S. Cl.
CPC . *A61B 8/14* (2013.01); *A61B 8/463* (2013.01); *A61B 8/00* (2013.01); *A61B 8/06* (2013.01); *A61B 8/13* (2013.01); *A61B 8/483* (2013.01)

(58) Field of Classification Search
CPC .............. A61B 8/00; A61B 8/06; A61B 8/13; A61B 8/463; A61B 8/483
USPC .......................... 600/437, 443, 454, 480, 504
See application file for complete search history.

(56) References Cited

U.S. PATENT DOCUMENTS

| | | | |
|---|---|---|---|
| 5,443,071 A * | 8/1995 | Banjanin et al. | 600/455 |
| 5,474,073 A * | 12/1995 | Schwartz et al. | 600/456 |
| 5,879,302 A | 3/1999 | Hashimoto et al. | |
| 6,102,864 A | 8/2000 | Hatfield et al. | |
| 6,126,603 A | 10/2000 | Hatfield et al. | |

(Continued)

FOREIGN PATENT DOCUMENTS

| | | |
|---|---|---|
| EP | 1152364 A2 | 11/2001 |
| EP | 1189074 A2 | 3/2002 |

(Continued)

OTHER PUBLICATIONS

European Search Report dated Sep. 2, 2010, issued in related European Patent Application 08012536.2.

(Continued)

*Primary Examiner* — Vani Gupta
(74) *Attorney, Agent, or Firm* — Westerman, Hattori, Daniels & Adrian, LLP (57) ABSTRACT

An ultrasound diagnostic apparatus which forms a three-dimensional bloodstream image by reference to volume data obtained from a three-dimensional space within a living organism. A modified maximum value detection method is applied along each ray. Search of a maximum value is sequentially executed from a search start point, and at a time point when a predetermined termination condition is satisfied, a maximum value which is being detected at this time point is regarded as a specific maximum value. The specific maximum value is then converted into a pixel value. The specific maximum value is a first peak and is specified even if a higher peak exists after the first peak. A three-dimensional bloodstream image is formed by a plurality of pixel values. In a portion of the three-dimensional bloodstream image in which two bloodstreams cross each other, a bloodstream located on the front side is preferentially displayed.

7 Claims, 4 Drawing Sheets

(56) References Cited

U.S. PATENT DOCUMENTS

| | | | |
|---|---|---|---|
| 6,249,693 B1* | 6/2001 | Cline et al. | 600/410 |
| 6,312,385 B1 | 11/2001 | Mo et al. | |
| 6,322,509 B1 | 11/2001 | Pan et al. | |
| 6,334,847 B1 | 1/2002 | Fenster et al. | |
| 6,352,509 B1 | 3/2002 | Kawagishi et al. | |
| 6,423,006 B1 | 7/2002 | Banjanin | |
| 6,438,403 B1* | 8/2002 | Cline et al. | 600/410 |
| 6,503,202 B1 | 1/2003 | Hossack et al. | |
| 6,547,731 B1* | 4/2003 | Coleman et al. | 600/455 |
| 7,147,602 B2* | 12/2006 | Muramatsu et al. | 600/504 |
| 7,448,998 B2* | 11/2008 | Robinson | 600/447 |
| 2003/0191399 A1* | 10/2003 | Muramatsu et al. | 600/480 |
| 2005/0033174 A1* | 2/2005 | Moehring et al. | 600/453 |
| 2006/0184021 A1 | 8/2006 | Kim et al. | |
| 2006/0184029 A1 | 8/2006 | Haim et al. | |
| 2006/0241460 A1* | 10/2006 | Kimura et al. | 600/454 |
| 2008/0004527 A1* | 1/2008 | Coleman et al. | 600/437 |
| 2008/0009727 A1 | 1/2008 | Kataguchi | |
| 2008/0287799 A1* | 11/2008 | Hall et al. | 600/454 |
| 2009/0024033 A1 | 1/2009 | Murashita | |

FOREIGN PATENT DOCUMENTS

| | | |
|---|---|---|
| JP | 10-171976 A | 6/1998 |
| JP | 2000-210289 A | 8/2000 |
| JP | 2000-237192 A | 9/2000 |
| JP | 2001-17428 A | 1/2001 |
| JP | 2002-008004 A | 1/2002 |
| JP | 2002-052026 A | 2/2002 |
| JP | 2004-215701 A | 8/2004 |
| JP | 2005-40622 A | 2/2005 |
| JP | 2005-157664 A | 6/2005 |
| JP | 2006-51202 A | 2/2006 |
| WO | 2006/086442 A2 | 8/2006 |

OTHER PUBLICATIONS

Bullitt, Elizabeth et al.; "vol. Rendering of Segmented Tubular Objects"; Lecture Notes in Computer Science 2208, Jan. 1, 2001, p. 161-168.

Partial European Search Report, issued May 17, 2010 for corresponding European Patent Application No. 08012537.0.

Mroz, Lukas et al.; "Maximum Intensity Projection at Warp Speed"; Computers and Graphics, Jun. 1, 2000, p. 343-352, vol. 24 No. 3.

Partial European Search Report, issued May 12, 2010 for corresponding European Patent Application No. 08012536.2.

McInerney, Tim et al.; "Deformable Models in Medical Image Analysis"; Proceedings of the IEEE Workshop on Mathematical Methods in Biomedical Image Analysis, Jun. 21, 1995, p. 171-180.

Office Action dated Feb. 3, 2011 issued in co-pending U.S. Appl. No. 12/174,123.

Extended European Search Report dated Apr. 29, 2011, issued in corresponding European Patent Application No. 08012537.0.

European Office Action dated Jul. 13, 2011, issued in corresponding European Patent Application No. 08012536.2.

Notice of Grounds for Rejection mailed on Feb. 21, 2012, issued in corresponding Japanese Patent Application No. 2007-185566.

* cited by examiner

ULTRASOUND DIAGNOSTIC APPARATUS

BACKGROUND

1. Technical Field

The present invention relates to an ultrasound diagnostic apparatus, and more particularly to a technology of forming a three-dimensional bloodstream image.

2. Related Art

In the medical field, an ultrasound diagnostic apparatus transmits and receives ultrasonic waves to and from a living organism and generates an ultrasound image on the basis of a reception signal obtained by transmission and reception of the ultrasonic waves. Typical ultrasound images may include a two-dimensional tissue image, which is a monochrome image (B-mode image), and a two-dimensional bloodstream image, which is a color image. A two-dimensional bloodstream image is color representation of Doppler components or motion information (e.g., velocity information, power information, and so on) which are contained in a reception signal. A two-dimensional tissue image may be formed by reference to the motion information. In general, a two-dimensional tissue image and a two-dimensional bloodstream image are combined to form a combined image, which is then to be displayed on a display.

In recent years, three-dimensional ultrasound diagnostic apparatuses which form a three-dimensional tissue image by reference to volume data obtained by transmission and reception of ultrasonic waves with respect to a three-dimensional space within a living organism have been in wide-spread use. Conventionally, a three-dimensional tissue image is formed by using a volume rendering method, for example, and is a stereoscopic representation of a tissue (e.g. an organ) within a living organism. Meanwhile, motion volume data can be obtained by extracting motion information from volume data. Here, motion volume data refers to three-dimensional data formed of the motion information. By applying three-dimensional image processing to the motion volume data, a three-dimensional bloodstream image can be formed.

JP 2005-157664 A (Reference 1), JP 2005-40622 A (Reference 2), JP 2006-51202 A (Reference 3), and JP 2001-17428 A (Reference 4) disclose conventional ultrasound diagnostic apparatuses which form a three-dimensional ultrasound image.

In a case where the magnitude of velocity or power is represented by the level of brightness in forming a three-dimensional bloodstream image, provided that a bloodstream located on the front side is a low-velocity stream and a bloodstream on the further back side is a high-velocity stream, the high-velocity bloodstream located on the back side is represented with a high brightness and the low-velocity bloodstream located on the front side is represented with a low brightness, or only the high-velocity bloodstream on the back side is represented. Consequently, the resulting image loses a sense of depth, which is a characteristic of a three-dimensional image. If a weighting function is applied in the depth direction in order to prevent the above disadvantage, the magnitude of motion information such as velocity cannot be represented in an accurate manner. As such, formation of a three-dimensional bloodstream image suffers from specific problems which are inherent thereto and differ from those regarding formation of a three-dimensional tissue image.

SUMMARY

The present invention advantageously provides an ultrasound diagnostic apparatus which is capable of forming a three-dimensional bloodstream image in which a sense of depth can be achieved.

The present invention also advantageously provides an ultrasound diagnostic apparatus which is capable of accurately representing the magnitude of bloodstream information.

In accordance with one aspect of the present invention, there is provided an ultrasound diagnostic apparatus including a unit which transmits and receives ultrasonic waves with respect to a three-dimensional space within a living organism to thereby obtain original volume data, a generation unit which removes noise from the original volume data to generate bloodstream volume data, and an image-forming unit which forms a three-dimensional bloodstream image by reference to the bloodstream volume data, wherein the image-forming unit searches for a specific maximum value which is a first peak value found first from a search start point on each of a plurality of rays set with respect to the bloodstream volume data, the specific maximum value on each ray corresponding to a pixel value concerning each ray, and the three-dimensional bloodstream image is formed by reference to a plurality of pixel values corresponding to the plurality of rays.

With the above structure, when forming a three-dimensional bloodstream image by reference to the bloodstream volume data, for each ray, a voxel value (motion information) is sequentially referred to starting from the search start point to search for the specific maximum value (a representative value). More specifically, on each ray, the first peak value is determined as the specific maximum value, which is then reflected in a pixel value. The three-dimensional bloodstream image is formed of a plurality of pixel values obtained for a plurality of rays. The motion information preferably represents a positive or negative velocity or a power (i.e., information corresponding to an absolute value of the velocity). The motion information may be Doppler information, or may be in the form of a two-dimensional or three-dimensional vector. If the three-dimensional bloodstream image is a velocity image, preferably, the direction of flow is represented with different hues and the magnitude of velocity is represented by the level of brightness. The search start point is a point which is set on a viewpoint (a ray original point) or is set on the further back side away from the viewpoint. The viewpoint may be set arbitrarily.

According to the conventional maximum value method, because in a portion where two bloodstreams cross each other, an absolute maximum value on the ray is unconditionally imaged, there are cases in which the bloodstream located on the back side is preferentially represented. This results in a problem that a sense of depth is lost. According to the present invention, on the other hand, because a modified maximum value method is realized; that is, basically, because a first peak is always imaged, the bloodstream on the front side can be preferentially represented in the above-described portion where the bloodstreams cross each other, so that a sense of depth can be retained. Further, because it is not necessary to apply special weighting processing along the depth direction, the motion information can be represented in an accurate manner. However, in addition to the above modified method, a weighting processing may be applied along the depth direction for the purpose of enhancing stereoscopic vision, and so on. Here, the first peak value, which corresponds to a center of the bloodstream located on the front side, may be a value corresponding to a vertex, or a local average value in the vicinity of a vertex.

Preferably, when a predetermined termination condition is satisfied during the course of executing maximum value search processing sequentially for each voxel starting from the search start point on each ray, a maximum value which is detected at this time is regarded as the first peak value. Preferably, the predetermined termination condition is a condition that, in the course of sequentially executing the maximum value search processing while a voxel value of each voxel is being referred to, the voxel value first increases and then decreases, and further reaches a predetermined value.

If a plurality of hills are present in a graph (a series of voxel values) along the ray, the vertex of the first hill, for example, corresponds to the first peak value described above. However, whether or not the vertex corresponds to the first peak value can generally be determined when the search has progressed to such a point that a search point has passed over the vertex of the first hill and then descended a negative gradient or when the search has further progressed to such a point that the search point has reached the bottom of a valley. In either case, it is desirable to set the termination condition so as to allow specification of the first peak without fail (that is, so as not to specify the second or later peak) and also to allow execution of a search operation as simply and rapidly as possible. It is desirable to terminate the search operation concerning the target ray at a time point when the first peak is specified.

Preferably, on the three-dimensional bloodstream image, in a portion in which an image of a bloodstream located on a front side and an image of a bloodstream located on a further back side cross each other, the image of the bloodstream located on the front side is preferentially represented. Preferably, on the three-dimensional bloodstream image, a center portion of a bloodstream is represented with a higher priority and with a higher brightness as compared with a peripheral portion around the center portion of the bloodstream. As the pixel value is determined by the first peak, the bloodstream on the front side as seen from the viewpoint is preferentially displayed. On similar grounds, when distribution of the velocity (or power) is generated in the bloodstream, the maximum velocity (or the maximum power) in the distribution is preferentially represented. Namely, on each ray, a center portion of the bloodstream is represented with a higher priority than the peripheral portion around the center portion of the bloodstream.

Preferably, the generation unit includes a computation unit which generates motion volume data from the original volume data, an identification unit which generates identification data for distinguishing between a bloodstream portion and a noise portion by reference to the motion volume data, and an extraction unit which extracts the bloodstream volume data from the motion volume data by reference to the identification data. In a three-dimensional bloodstream image, in which noises are imaged, it is difficult to recognize the running state of a bloodstream. Accordingly, in the present invention, the bloodstream volume data in which noises are effectively removed or reduced are generated, and a three-dimensional bloodstream image is formed by reference to the bloodstream volume data.

Preferably, the identification unit specifies a plurality of objects included in the motion volume data, and identifies a type of each of the objects which are specified, by reference to the size of the object to thereby generate the identification data. While it is difficult to discriminate between a bloodstream portion and a noise portion by reference to the motion components, with this structure, these portions can be distinguished from each other in accordance with their spatial sizes.

In accordance with another aspect of the present invention, there is provided an image-processing program to be executed in a computer, for forming a three-dimensional bloodstream image by reference to bloodstream volume data, the image-processing program comprising a module which searches for a specific maximum value which is a first peak value first found from a search start point on each of a plurality of rays set with respect to the bloodstream volume data, a module which associates the specific maximum value on each ray with a pixel value concerning the ray, and a module which forms a three-dimensional bloodstream image by reference to a plurality of pixel values corresponding to the plurality of rays. Each module described above corresponds to a specific software function or a program portion for implementing the specific function. The program according to the present invention is provided via a storage medium or a network and is installed in a computer. The storage medium includes a medium such as a CD-ROM, and so on. Here, the above-described computer is a general personal computer or an ultrasound diagnostic apparatus, for example. The three-dimensional bloodstream image may be formed by reference to the volume data which are obtained in real time or by reference to the volume data which are stored.

BRIEF DESCRIPTION OF THE DRAWINGS

A preferred embodiment of the present invention will be described in detail by reference to the following figures, wherein.

DETAILED DESCRIPTION

A preferred embodiment of the present invention will be described in detail with reference to the accompanying drawings.

Figure 1:
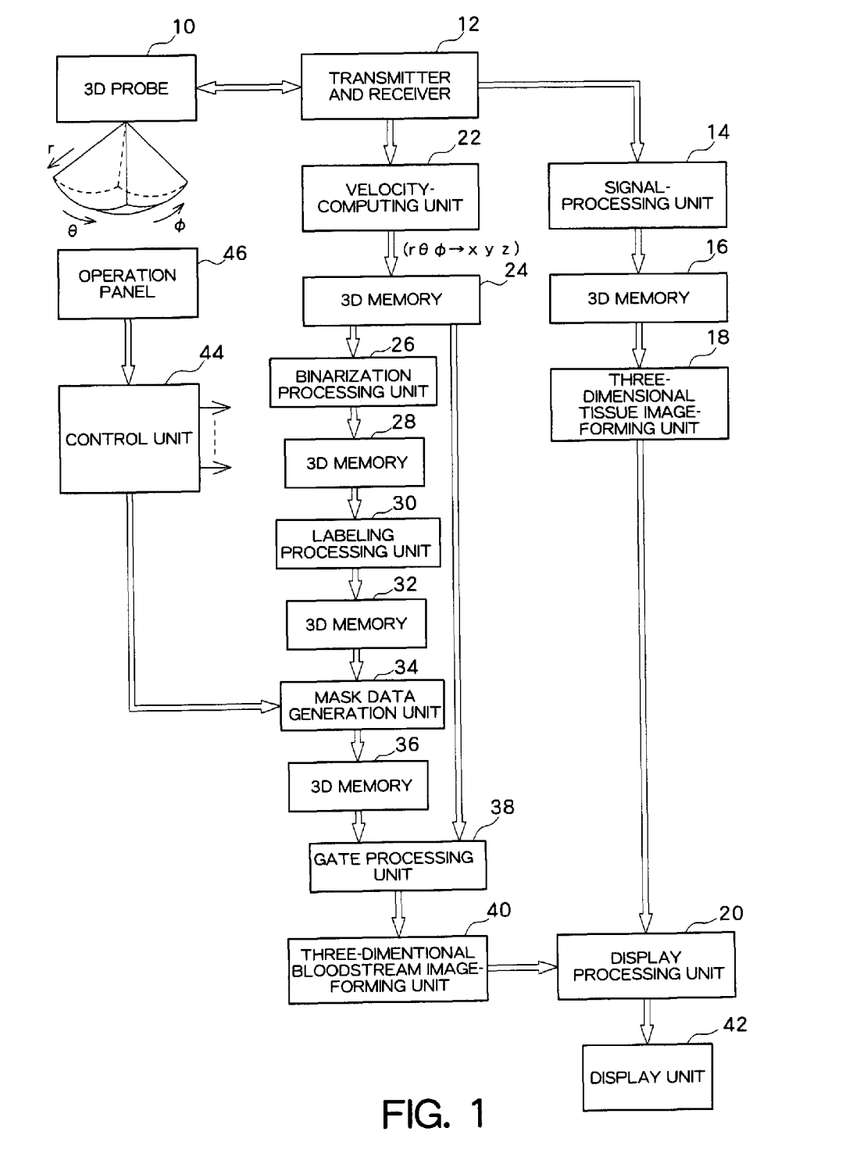
FIG. 1 is a block diagram showing an ultrasound diagnostic apparatus according to a preferred embodiment of the present invention.

FIG. 1 is a block diagram showing the overall structure of an ultrasound diagnosis apparatus according to a preferred embodiment of the present invention. The ultrasound diagnostic apparatus according to the present embodiment is for use in the medical field, and includes a function of forming a three-dimensional bloodstream image which is a stereoscopic representation of bloodstream within a living organism.

In the present embodiment, a 3D (three-dimensional) probe 10 includes a 2D (two-dimensional) array transducer. The 2D array transducer includes a plurality of transducer elements which are arranged two-dimensionally. An ultrasound beam is formed by the 2D array transducer and is electronically scanned. Known electronic scan methods include electronic sector scan, electronic linear scan, and others. In FIG. 1, a symbol "r" indicates the depth direction, which corresponds to the ultrasound beam direction. Symbols "θ" and "φ" represent directions in which an ultrasound beam is scanned. In the illustrated example, a pyramid-shaped echo data acquisition region, which is a three-dimensional space constructed within a living organism, is formed. Here, in place of the 2D array transducer, a 1D array transducer and a mechanism for mechanically scanning the 1D array transducer may be provided.

A unit 12 functions as a transmitting beam former transmitter and a receiving beam former receiver. The unit 12, at the time of transmission, provides a plurality of transmission signals, in parallel, to the 2D array transducer, thereby forming a transmitting beam. At the time of reception, a reflection wave from within the living organism is received by the 2D array transducer, which outputs a plurality of reception signals, in parallel, to the unit 12. The unit 12 then performs phase adjustment and summation processing with respect to the plurality of reception signals to thereby electronically form a receiving beam. In this case, a reception dynamic focus technology is applied. According to the present embodiment, the reception signal (beam data) having been subjected to beam adjustment and summation is output to a signal-processing unit 14 and a velocity-computing unit 22. Here, an ultrasound beam for forming a three-dimensional tissue image and an ultrasound beam for forming a three-dimensional bloodstream image may be formed separately.

The signal-processing unit 14 is a module which executes signal processing for forming a three-dimensional tissue image, and has functions such as detection processing, logarithmic compression processing, and so on. The beam data having been subjected to the signal processing are stored in a 3D memory 16. Here, when storing and reading data with respect to the 3D memory 16, coordinate transformation processing is executed. In the present embodiment, a three-dimensional tissue image-forming unit 18 forms a three-dimensional tissue image from volume data stored in the 3D memory 16, by means of a volume rendering method in which opacity is used. More specifically, a plurality of rays are set with respect to the volume data, and, for each ray, a voxel computation is sequentially repeated along the ray to thereby determine a pixel value. The image data of the three-dimensional tissue image are output to a display processing unit 20. The image data are then provided to a display unit 42, which displays the three-dimensional tissue image.

Now, processing for forming a three-dimensional bloodstream image will be described in detail. The three-dimensional bloodstream image is displayed separately from or in combination with the three-dimensional tissue image described above.

The velocity-computing unit 22, in the present embodiment, includes a quadrature detector, a low-velocity motion removal filter, an autocorrelation operator, a velocity operator, and so on. Specifically, the velocity-computing unit 22 has a function of computing the velocity information as one type of motion information contained in a reception signal. More specifically, the velocity-computing unit 22 extracts Doppler components contained in a reception signal, applies an autocorrelation operation with respect to the Doppler components, and further computes the velocity (the average velocity) from the autocorrelation result. The velocity which is obtained in this case has a positive or negative sign. The velocity information is computed for each voxel. Although the velocity is obtained as the motion information in the present embodiment, a power (or an absolute value of the velocity) may be computed. Further, although in the present embodiment the velocity information along the beam direction is obtained, a two-dimensional velocity vector or a three-dimensional velocity vector may be computed.

The velocity data output from the velocity-computing unit 22 are stored in a 3D memory 24. Then, when writing or reading the data with respect to the 3D memory 24, coordinate transformation is executed. In this case, coordinate transformation from the rθφ coordinate system to the XYZ coordinate system is executed. The 3D memory 24 has a storage space corresponding to the three-dimensional space within the living organism described above. The 3D memory 24 stores velocity volume data (motion volume data) formed as an aggregate of velocity data which are voxel data. Here, each of 3D memories 28, 32, and 36, which will be described below, preferably has a storage space similar to that of the 3D memory 24 and functions as a buffer memory.

A binarization processing unit 26 is a module which executes binarization processing with respect to the velocity volume data stored in the 3D memory 24. Specifically, there is executed processing in which a voxel value which is smaller than a predetermined threshold value is replaced with 0 (an invalid value) and a voxel value which is equal to or greater than the predetermined threshold value is replaced with 1 (a valid value). As a result, only the voxel values which are candidates of bloodstreams are specified. The volume data having been subjected to this binarization processing are binary volume data, which are also one type of the motion volume data. The binary volume data are stored in the 3D memory 28.

A labeling processing unit 30 applies three-dimensional labeling processing to the binary volume data, as will be described with reference to FIG. 2. Specifically, the labeling processing unit 30 extracts a voxel aggregation (i.e. an object) having a voxel value 1. In general, a plurality of bloodstreams and a plurality of noises exist within a three-dimensional space, and a plurality of objects are specified as a result of the labeling processing. Each object is composed of a plurality of voxels which are spatially coupled to each other. In this embodiment, these voxels have a voxel value, which is 1. Although an object composed of one isolation voxel may be extracted, such an object is a noise and need not be extracted. Further, the minimum number of voxels forming an object may be defined. Here, the three-dimensional labeling processing itself is a known technology. The volume data having been subjected to the three-dimensional labeling processing or the data of processing results are stored in the 3D memory 32.

Here, with the labeling processing, an object number is assigned to each object, and the number of voxels constituting each object is counted to obtain a count value. The object number and the count value constitute object attribute information.

A mask data generation unit 34 reads out from the 3D memory 32 the volume data and the attribute information obtained as a result of the three-dimensional labeling processing, and executes processing for identifying the type of each object. Namely, the mask data generation unit 34 identifies whether each object is a bloodstream (which is a subject to be imaged) or noise (which is not a subject to be imaged). More specifically, the mask data generation unit 34 compares the number of voxels of each object with a predetermined reference value, and determines an object with the number of voxels which is smaller than the reference value as noise and determines an object with the number of voxels which is equal to or greater than the reference value as a bloodstream. In general, the volume size of noise is smaller than the volume size of a bloodstream within a three-dimensional space. Accordingly, although it is difficult to discriminate noise and bloodstream by reference to the magnitude of velocity, it is possible to distinguish between a noise portion and a bloodstream portion by reference to a difference in the spatial size. For this identification, the count value which is obtained in the three-dimensional labeling processing described above; that is, a volume size, is referred to.

The mask data generation unit 34 generates, for each object, identification data (mask data) representing an identification result of whether the object is a bloodstream or noise. The mask data is three-dimensional volume data, which are reference data which can be used for spatially identifying a portion corresponding to noise and a portion corresponding to a bloodstream.

Here, the mask data which identify an object corresponding to noise can be generated if noise removal is performed in gate processing which will be described below, whereas the mask data which identifies an object corresponding to bloodstream can be generated if extraction of bloodstream is performed in the gate processing. The mask data generated by the mask data generation unit 34 are stored in the 3D memory 36.

A gate-processing unit 38, with the use of the mask data described above, applies bloodstream extraction processing (and/or a noise removal processing) to the motion volume data which are read from the 3D memory 24, and generates, as a result, volume data which basically represent only bloodstreams; i.e., bloodstream volume data, which are then provided to a three-dimensional bloodstream image-forming unit 40.

The three-dimensional bloodstream image-forming unit 40, in the present embodiment, generates a three-dimensional bloodstream image by means of the maximum value method. However, a modified maximum value method is applied in the present embodiment, as will be specifically described below with reference to FIGS. 3 to 5. With the modified maximum value detection method according to the present embodiment, in a portion in which a plurality of bloodstreams cross each other, a bloodstream located on the front side as seen from the viewpoint, which is a bloodstream located closer to the viewpoint, can be represented preferentially, or high-velocity components in the bloodstream can be represented preferentially, so that a clear three-dimensional bloodstream image can be advantageously formed without losing the sense of depth.

The display processing unit 20 has a color processing function, an image-combining function, and so on. The display processing unit 20 outputs image information which is selected in accordance with a display mode set by a user and provides the image information to the display unit 42. In the present embodiment, the three-dimensional tissue image is displayed as a monochrome image, whereas the three-dimensional bloodstream image is displayed as a color image. The three-dimensional bloodstream image is a velocity image in which a bloodstream approaching the probe is represented with red hue and a bloodstream moving away from the probe is represented with blue hue, and also, different velocities are represented by brightness of the respective hues. The display processing unit 20 performs such a coloring processing. As described above, because a bloodstream located on the front side seen from the viewpoint is represented preferentially in a portion in which a plurality of bloodstreams cross each other, problems such as a loss of the sense of depth and unnatural mixture of red and blue colors in a portion where bloodstreams cross each other can be eliminated or alleviated. Also, as a stream with the highest velocity in the center portion of the bloodstream can be represented preferentially due to the method which will be described below, the state of each bloodstream can be advantageously represented in a clear manner.

As a matter of course, the method according to the present invention can be similarly applied to a case in which a power image is displayed as a three-dimensional bloodstream image. A power image is formed as an image of a red color, for example, in which the magnitude of power is represented by brightness. In either case, there can be formed a three-dimensional bloodstream image in which noise, especially undesirable clutter generated due to interference of ultrasonic waves or the like, is effectively reduced.

A control unit 44, which performs operation control of each unit described in FIG. 1, is formed of a CPU and an operation program. An operation panel 46 is connected to the control unit 44. The operation panel 46 includes a keyboard and a trackball and is operated by a user to set the operation conditions and parameters. Here, the function of each of the binarization processing unit 26, the labeling processing unit 30, the mask data generation unit 34, the gate processing unit 38, the three-dimensional image-forming unit 40, the display processing unit 20, and so on, can be essentially implemented as a software function. It is also possible to output the information stored in the 3D memory 24 to an external personal computer and execute the processing described above on the personal computer to thereby form a three-dimensional bloodstream image.

Each of the 3D memories 24 and 16 can be formed as a cine memory having a ring buffer structure. A three-dimensional bloodstream image may be formed as a moving image based on the time-sequential volume data stored over a fixed time period.

Figure 2:
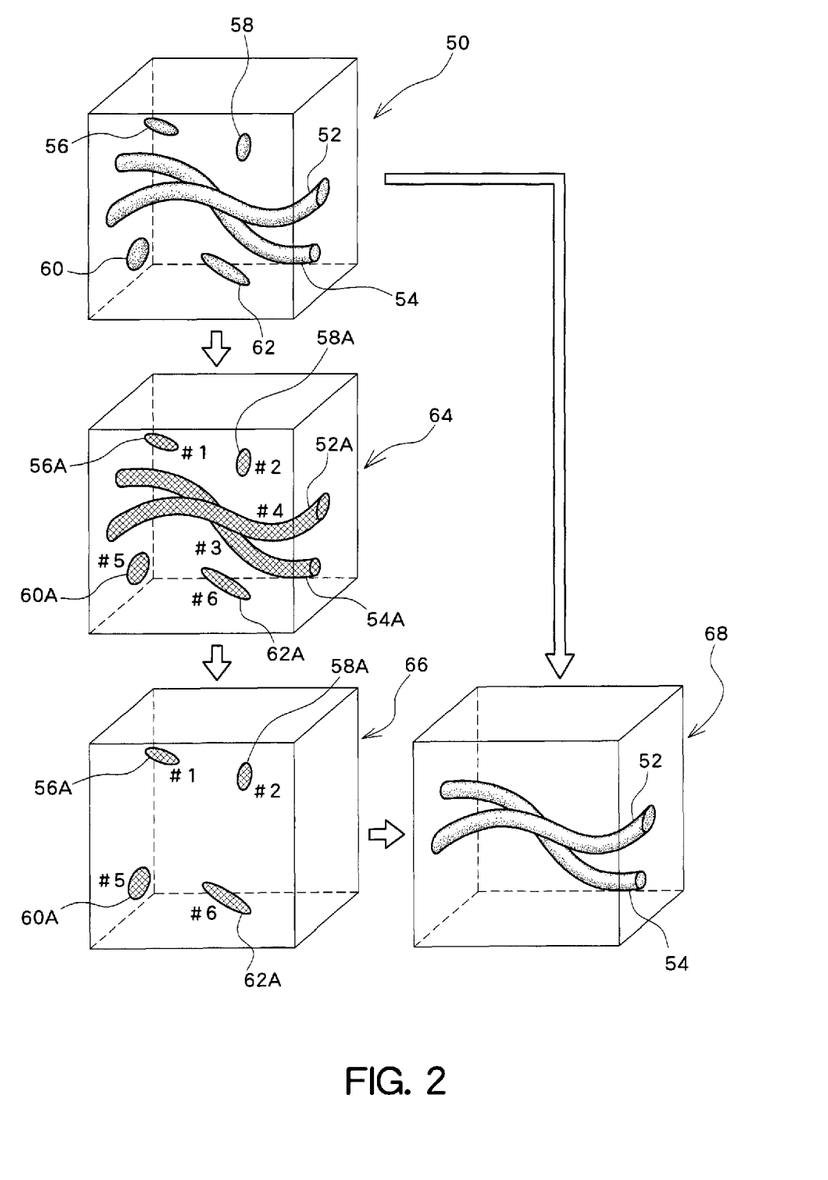
FIG. 2 is a conceptual view for explaining processing for generating bloodstream volume data.

FIG. 2 conceptually shows processing of generating bloodstream volume data. Reference numeral 50 indicates velocity volume data. In this example, portions 52 and 54 corresponding to bloodstreams and portions 56, 58, 60, and 62 corresponding to noises are present within a three-dimensional space.

A result of application of the binarization processing, and then the three-dimensional labeling processing, to the velocity volume data 50 is shown by a view indicated by reference numeral 64. With the binarization processing, a value of 1 is assigned to each voxel forming each of the portions 52, 54, 56, 58, 60, and 62 described above, and a value of 0 is assigned to other voxels. More specifically, in the binarization processing, a predetermined threshold value is set, and a voxel value which is smaller than the threshold value is replaced with 0 and a voxel value which is equal to or greater than the threshold value is replaced with 1, so that a still object and a low-velocity object can be advantageously excluded from the subjects to be processed. As required, various filtering processing operations can be applied to the binarized volume data. Then, with the labeling processing, a plurality of objects 52A, 54A, 56A, 58A, 60A, and 62A which spatially exist are specified. Here, each object is an aggregate of voxels which are spatially contiguous and which have a value 1. An object formed of a single voxel can also be identified. Object numbers #1 to #6 are assigned to the respective objects in a predetermined order. Also, the number of voxels forming each object is counted. Namely, in the three-dimensional labeling processing, at the time of extracting an object, counting of voxels forming the object is executed and the resulting count value is stored as attribute information representing the volume size of the object.

As described above, in view that a bloodstream object generally has a larger volume size whereas a noise object generally has a smaller volume size, it is possible to discriminate between a bloodstream portion and a noise portion. In the example shown in FIG. 2, four noise portions are identified, and these noise portions form three-dimensional mask data 66. In this case, the portions 56A, 58A, 60A, and 62A designated by object numbers #1, #2, #5, and #6, respectively, are specified.

Once the three-dimensional mask data are generated as described above, the three-dimensional mask data 66 are caused to operate on the velocity volume data, and more specifically, a logical operation is performed between the three-dimensional mask data and the velocity volume data, to thereby remove the noise portions 56, 58, 60, and 62 contained in the velocity volume data 50, so that bloodstream volume data 68 in which noise is removed can be generated. The bloodstream volume data 68 basically include only the portions 52 and 54 corresponding to the bloodstreams. Accordingly, by executing rendering processing based on the bloodstream volume data, there can be provided a three-dimensional bloodstream image in which noises are effectively reduced, or the bloodstreams are clearly represented.

Although, in the example shown in FIG. 2, the portions 56A, 58A, 60A, and 62A are identified by the three-dimensional mask data 66 as the subjects to be excluded, various other methods may also be applied for configuring the three-dimensional mask data 66. For example, three-dimensional mask data for extracting the bloodstream portions may be configured. In any case, control data which can be used for achieving removal of noise portions and extraction of bloodstream portions are generated.

Figure 3:
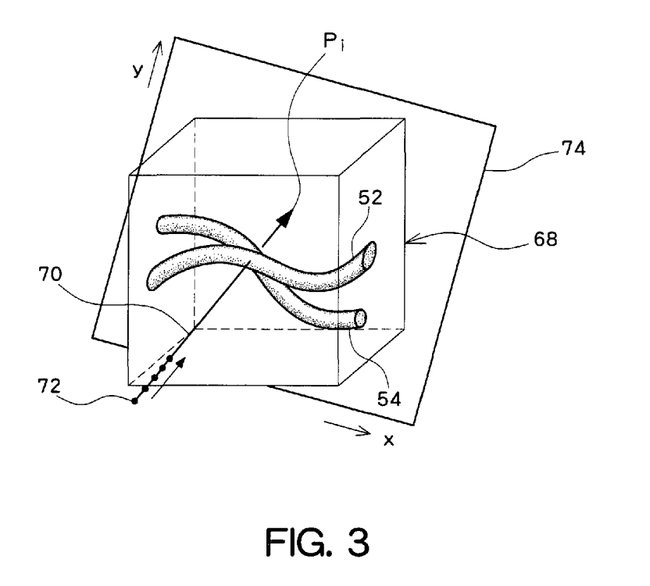
FIG. 3 is a conceptual view for explaining a relationship between the bloodstream volume data and a screen.
Figure 4:
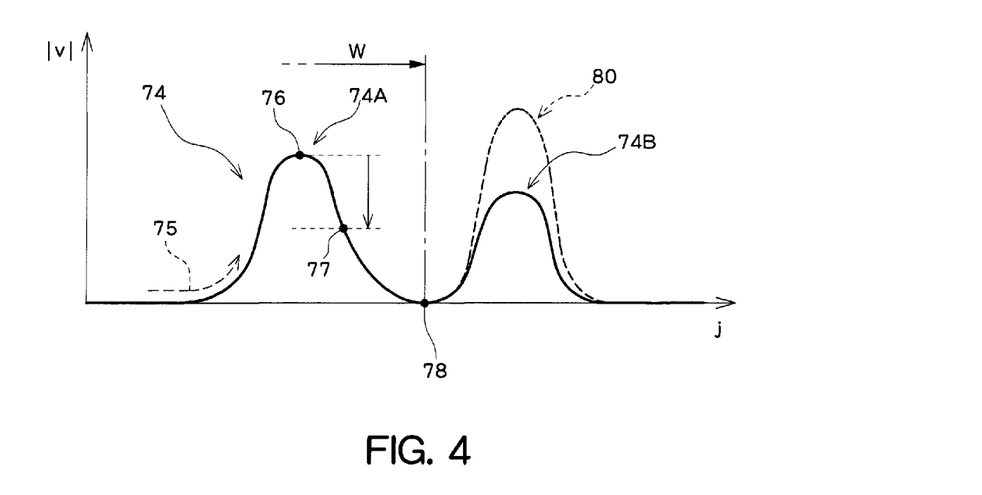
FIG. 4 is a chart (graph) showing distribution of voxel values along a ray.
Figure 5:
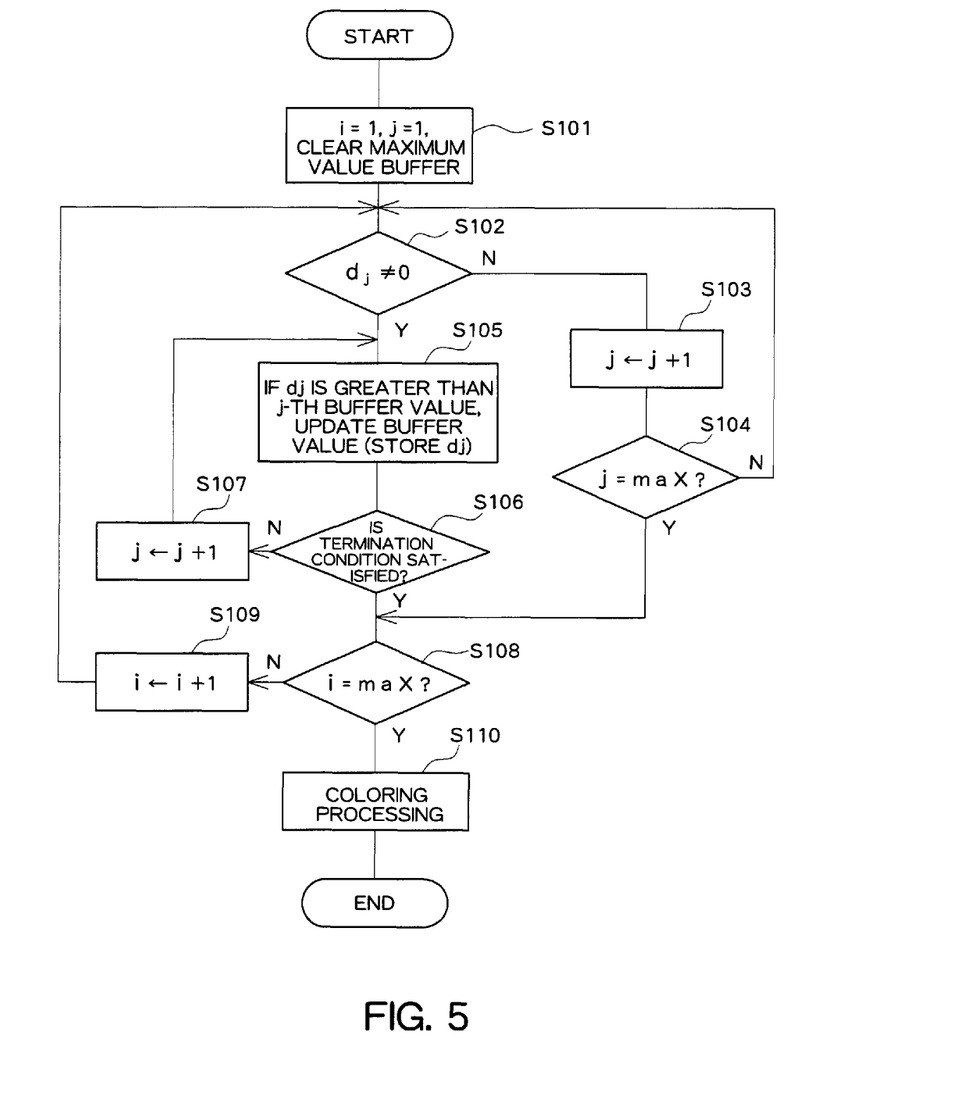
FIG. 5 is a flowchart showing processing for forming a three-dimensional bloodstream image.

Referring now to FIGS. 3 to 5, processing for forming a three-dimensional bloodstream image will be described.

FIG. 3 shows the bloodstream volume data 68. A modified maximum value detection method, which will be described below, is to be applied to the bloodstream volume data 68. First, a plurality of virtual rays (lines of sight) are set with respect to the bloodstream volume data 68. Here, a viewpoint 72 can be set at an arbitrary position. In the example shown in FIG. 3, only one representative ray 70 is shown. The plurality of rays may be parallel to each other or non-parallel. For each ray, an operation which will be described below is executed to determine one pixel value. By mapping, on a screen 74, a plurality of pixel values which are obtained for the plurality of rays, a three-dimensional bloodstream image can be formed.

Now, with regard to the ray 70, voxel values are sequentially obtained in the order of voxels on the ray 70, starting from the viewpoint 72. Namely, a maximum value search processing is executed. Here, it is desired that the voxel value is an absolute value of the velocity, in order to specify the bloodstream on the front side, regardless of the direction of the stream (i.e. regardless of a negative sign or a positive sign). In the example shown in FIG. 3, the ray 70 penetrates both the portion 52 corresponding to a bloodstream and the portion 54 corresponding to a bloodstream, and is associated with a specific address Pi on the screen 74.

FIG. 4 shows, in a graph, a sequence of voxel values existing on the ray described above. The left end of the horizontal axis represents the viewpoint or a search start point, and the direction to the right from the viewpoint represents the depth direction. Further, the vertical axis represents the magnitude of a voxel value, which is an absolute value of the velocity in the present embodiment. Specifically, although, in the actual display of an image, each bloodstream is represented with a hue in accordance with the direction of the stream in consideration the positive or negative sign, the sign should not be considered when specifying the peak of the bloodstream located on the front side, and therefore an absolute value of the velocity is referred to. Here, when the voxel value corresponds to a power, the voxel value is directly referred to for performing search of the maximum value.

The graph shown in FIG. 4 includes two hills 74A and 74B. The first hill 74A corresponds to the bloodstream 52 located on the front side in FIG. 3, and the following hill 74B corresponds to the bloodstream 54 located on the further back side in FIG. 3. Once search of the maximum value is started from the search start point, the voxel values are sequentially referred to along the j direction or the depth direction as indicated by reference numeral 75. Then, as will be described below with reference to FIG. 5, the current voxel value which is being referred to is compared with the current maximum value stored in a buffer. If the current voxel value is greater than the current maximum value, the maximum value stored in the buffer is updated; i.e., the current voxel value is written in the buffer. With sequential repetition of this processing, after the voxel value of the first peak 76 corresponding to the vertex of the first hill 74A is stored in the buffer, the buffer value remains unupdated, and the reference position descends a slope of the hill 74A.

In the present embodiment, if the voxel value increases and then decreases to finally reach 0 in the course of search; i.e., if the voxel value reaches a point indicated by reference numeral 78, the maximum value search processing is completed. At this point in time, the maximum value currently stored in the buffer is identified as a specific maximum value, and is then converted into a pixel value. In this shown example, the value of the first peak 76 is identified as the specific maximum value.

Accordingly, the second hill 74B is not considered as a search subject, because the search is completed before the second hill 74B. Consequently, in the portion in which the two bloodstreams cross each other, only the bloodstream located on the front side is displayed, thereby avoiding a problem that the bloodstream on the further back side is unnecessarily imaged.

Although in the present embodiment, the search is completed at the time point when the first hill is crossed to find the first valley, the search may be completed at a position 77 located at a predetermined level further down from the peak 76, for example. Alternatively, it is also possible to compute a gradient at each point and terminate the search at a point where the current gradient exceeds a predetermined value.

The present embodiment can provide an advantage that even if a second hill 80 is higher than the first hill 74A, the first peak 76, which is the vertex of the first hill 74A, can be specified reliably. However, the second or subsequent hill may be referred to for the purpose of preventing misidentification of the peak.

FIG. 5 shows, in a flowchart, a processing for forming a three-dimensional bloodstream image. First, in step S101, 1 is set as i, which represents a ray number, and also 1 is set as j, which represents a step number on the ray; i.e., a voxel address. Also, a maximum value buffer is cleared. In step S102, whether or not a currently-referred voxel value dj is 0 is determined. If dj is 0, the voxel which is currently being referred to is assumed to be located on the front side with respect to the first bloodstream. Then, in step S103, j is incremented by 1, and in step S104, whether or not j is a maximum value is determined. If j is determined to be a maximum value, processing in step S108 is executed in order to terminate the processing with regard to the ray which is currently noted. On the other hand, if j is not determined to be a maximum value in step S104, the processing proceeds to step S102.

If in step S102 it is determined that the voxel value dj is not 0, the processing in step S105 is performed. More specifically, a determination is made as to whether or not the voxel value dj which is currently being noted is greater than the j-th buffer value corresponding to the currently-noted ray. If the currently-noted voxel value dj is greater, there is executed update processing in which the current buffer value is replaced by the currently-noted voxel value dj. If the voxel value dj is equal to or smaller than the current buffer value, such update processing is not performed.

In step S106, whether or not a termination condition is satisfied is determined with regard to the current ray. As shown in FIG. 4, when the first hill is crossed and then the voxel value 0 is reached, it is determined that the termination condition is satisfied. Alternatively, other termination conditions may be applied. If the termination condition is not satisfied, processing proceeds to step S107, in which j is incremented by 1, and then step S105 and the subsequent steps are repeated. On the other hand, if it is determined that the termination condition is satisfied with regard to the currently-noted ray, then, in step S108, whether or not i, which is a ray number, reaches a maximum value is determined. Then, if it is determined that i does not reach the maximum value, i is incremented by 1 in step S109, and then step S102 and the subsequent steps described above are repeated.

On the other hand, if in step S108 it is determined that i reaches a maximum value, in step S110, coloring processing is applied to a three-dimensional bloodstream image formed of a plurality of pixel values which have been obtained until then. More specifically, hue and brightness are assigned in accordance with the direction and magnitude of the velocity, so that a three-dimensional bloodstream image, which is a color image, is formed.

In the three-dimensional bloodstream image, as described above with reference to FIG. 3, in a portion in which the bloodstreams cross each other, the bloodstream located on the front side seen from the viewpoint is preferentially displayed. In addition, when displaying each bloodstream, a center portion of the bloodstream with a higher velocity is displayed with a higher priority than a peripheral portion around the center portion of the bloodstream with a lower velocity, so that each bloodstream can be clearly displayed with a sense of depth. Further, with the above processing, high-speed computation can be executed, because the computation concerning the subject ray is completed if the first peak is specified and then the termination condition is satisfied. Although it is possible to apply weighting processing along the depth direction so as to prevent the bloodstream located on the deeper side from being displayed preferentially, such special and additional processing is not necessary according to the structure of the present embodiment. However, such a weighting processing in the depth direction may be performed for the purpose of image adjustment and so on.

As described above, the ultrasound diagnostic apparatus according to the present embodiment can advantageously generate bloodstream volume data in which noises (particularly clutter) present in a three-dimensional space are removed, and can further advantageously form a three-dimensional bloodstream image which is based on such bloodstream volume data and which also can provide a sense of depth and can faithfully represent motion information. The ultrasound diagnostic apparatus according to the present embodiment has two characteristics features (noise removal based on the object size, and image processing for preferentially displaying the bloodstream on the front side), which can be adopted independently from each other. It is possible, for example, to first generate the bloodstream volume data using the method as shown in FIG. 2, and then apply various known volume rendering methods to the bloodstream volume data. It is also possible to generate bloodstream volume data by using a general method and then apply the method described in FIGS. 3 to 5 to preferentially display the bloodstream located on the front side.

Although the preferred embodiment of the present invention has been described by reference to specific terms, such description is for illustrative purposes only, and it is to be understood that changes and variations may be made without departing from the spirit or scope of the appended claims.

What is claimed is:

1. An ultrasound diagnostic apparatus, comprising:
    a unit which transmits and receives ultrasonic waves with respect to a three-dimensional space within a living organism to thereby obtain original volume data;
    a generation unit which removes noise from the original volume data to thereby generate bloodstream volume data containing velocity information within a bloodstream; and
    an image-forming unit which forms a three-dimensional bloodstream image by reference to the bloodstream volume data,
    wherein the bloodstream volume data comprises a plurality of voxel values, each voxel value being a velocity value having a positive or negative sign;
    the image-forming unit comprises:
    a setting unit which, after the generation of the bloodstream volume data by the generation unit sets a plurality of rays radiating from a viewpoint, which is set at an arbitrary position, with respect to the bloodstream volume data generated by the generating unit, the plurality of rays being associated with addresses on a two-dimensional screen;
    a searching unit which searches a first peak value from a search start point as the viewpoint on each of the plurality of rays by sequentially referring to an absolute value of each of the voxel values; and
    a unit which forms the three-dimensional bloodstream image, in which the positive and negative signs are represented with different colors, by mapping, on the two-dimensional screen, the plurality of voxel values corresponding to a plurality of the first peak values searched on the plurality of rays,
    the searching unit executes a search process which sequentially refers to the absolute value of a voxel value of each voxel from the search start point on each of the plurality of rays, and in the search process, when the referred absolute value of the voxel value first increases, and then decreases after reaching a peak value corresponding to a vertex of a first hill, the peak value corresponding to the vertex of the first hill is determined as the first peak value, and
    on the three-dimensional bloodstream image, in a portion in which images of a plurality of bloodstreams cross each other, the image of the bloodstream closest to the viewpoint is preferentially represented.

2. The ultrasound diagnostic apparatus according to claim 1, wherein
    on the three-dimensional bloodstream image, a center portion of a bloodstream is represented with a higher priority and with a higher brightness as compared with a peripheral portion around the center portion of the bloodstream.

3. The ultrasound diagnostic apparatus according to claim 1, wherein the generation unit includes:
    a computation unit which generates motion volume data from the original volume data;
    an identification unit which generates identification data for distinguishing between a bloodstream portion and a noise portion based on the motion volume data; and
    an extraction unit which extracts the bloodstream volume data from the motion volume data by reference to the identification data.

4. The ultrasound diagnostic apparatus according to claim 3, wherein
    the identification unit specifies a plurality of objects included in the motion volume data, and identifies a type of each of the objects which are specified by reference to the size of the object to thereby generate the identification data.

5. The ultrasound diagnostic apparatus according to claim 4, wherein the identification unit applies three-dimensional labeling processing to the motion volume data to specify the plurality of objects.

6. The ultrasound diagnostic apparatus according to claim 1, wherein the three-dimensional bloodstream image is a color image, an image of a bloodstream flowing in a first direction is represented in a first color and an image of a bloodstream flowing in a second direction is represented in a second color, and in a portion on the three-dimensional bloodstream image in which an image of a bloodstream located on the front side and an image of a bloodstream located on the back side cross each other, the image of the bloodstream located on the front side is preferentially represented, so that mixture of the first color and the second color occurring in the portion in which the bloodstreams cross each other is prevented or reduced.

7. A non-transitory computer-readable storage medium having an image-processing program stored thereon which when executed in a computer forms a three-dimensional bloodstream image by reference to bloodstream volume data, wherein the bloodstream volume data comprises a plurality of voxel values, each voxel value being a velocity value having a positive or negative sign;

the image-processing program comprising:

obtaining original volume data;

removing noise from the original volume data to thereby generate the bloodstream volume data containing velocity information within a bloodstream;

after generating the bloodstream volume data, setting a plurality of rays radiating from a viewpoint, which is set at an arbitrary position, with respect to the generated bloodstream volume data, the plurality of rays being associated with addresses on a two-dimensional screen;

searching a first peak value from a search start point as the viewpoint on each of the plurality of rays by sequentially referring to an absolute value of each of the voxel values;

forming the three-dimensional bloodstream image, in which the positive and negative signs are represented with different colors, by mapping, on the two-dimensional screen, the plurality of voxel values corresponding to a plurality of the first peak values searched on the plurality of rays; and executing a search process which sequentially refers to the absolute value of a voxel value of each voxel from the search start point on each of the plurality of rays, and in the search process, when the referred absolute value of the voxel value first increases, and then decreases after reaching a peak value corresponding to a vertex of a first hill, the peak value corresponding to the vertex of the first hill is determined as the first peak value, and on the three-dimensional bloodstream image, in a portion in which images of a plurality of bloodstreams cross each other, the image of the bloodstream closest to the viewpoint is preferentially represented.

* * * * *